US006291720B1

(12) United States Patent
Smith et al.

(10) Patent No.: US 6,291,720 B1
(45) Date of Patent: Sep. 18, 2001

(54) SYNTHESIS OF GLYCOL ETHERS

(75) Inventors: Warren John Smith, Feltham (GB); Francois Clement Malherbe, East Malvern (AU)

(73) Assignee: BP Chemicals Limited, London (GB)

( * ) Notice: Subject to any disclaimer, the term of this patent is extended or adjusted under 35 U.S.C. 154(b) by 0 days.

(21) Appl. No.: 09/299,123

(22) Filed: Apr. 26, 1999

(30) Foreign Application Priority Data

Apr. 25, 1998 (GB) .................................................. 9808846

(51) Int. Cl.[7] ............................ C07C 41/09; C07C 41/01
(52) U.S. Cl. ......................... 568/618; 568/671; 568/672; 568/678; 568/679
(58) Field of Search ..................................... 568/671, 672, 568/678, 679, 618

(56) References Cited

U.S. PATENT DOCUMENTS 4,278,820 * 7/1981 Kametaka et al. .................... 568/678
5,256,828   10/1993 Cuscurida et al. .................... 568/620

FOREIGN PATENT DOCUMENTS

53037607 * 4/1978 (JP) .
92/11224   7/1992 (WO) .

* cited by examiner

Primary Examiner—Rosalynd Keys
(74) Attorney, Agent, or Firm—Nixon & Vanderhye

(57) ABSTRACT

This application relates to a process for making glycol ethers, said process comprising reacting an olefin oxide with an alcohol over a catalyst comprising a crystalline metallosilicate which is basic in character, wherein the molar ratio of alcohol to olefin oxide employed is at least 2:1.

10 Claims, No Drawings

SYNTHESIS OF GLYCOL ETHERS

This invention relates to a process for the synthesis of glycol ethers over basic zeolite catalysts.

Glycol ethers are versatile molecules which combine the best solvency features of alcohols and ethers. Glycol ethers have miscibility and solvency for a wide range of organic chemicals as well as water. For these reasons, glycol ethers figure prominently in the (i) surface coating industry as active solvents for resins, (ii) brake fluid industry as solvents, (iii) petroleum industry as anti-icers in various petroleum based fuels, (iv) automotive industry as anti-freezes and (v) speciality products for use in households. It is well known that such glycol ethers can be produced by the reaction of an alcohol with an olefin oxide in the presence of an acidic or basic catalyst.

One of the most widely studied inorganic materials for their catalytic activity are the cationic clays. These clays comprise negatively charged metal silicate sheets intercalated with hydrated cations, eg the smectite clays. Our prior published EP-A-0515636 describes the use of double hydroxide clays comprising magnesium and aluminium in their framework structure in their uncalcined form for producing glycol ethers by reacting an alcohol with an olefin oxide when such clays have an anion of the reactant alcohol incorporated in their interlamellar space. Such clays as synthesised normally have carbonate anions in the interlamellar space but this is exchanged with the anions of the reactant alcohol by conventional ion-exchange techniques. More recently, our prior published PCT/GB96/01462 discloses that hydrotalcite anionic clays having hydroxides of magnesium, aluminium, copper and/or chromium in their framework in addition to metal anions or (poly)oxometallate anions in the interlamellar space thereof, especially in their uncalcined form, are useful catalysts for producing glycol ethers. In this process the products invariably contain significant amounts polyethylene glycol as a by-product.

U.S. Pat. No. 5,256,828 describes a process for producing a narrow range glycol which comprises reacting a glycol with ethylene oxide in the presence of a metallosilicate catalyst. The document also mentions the possibility of alkoxylating alcohols, but it is silent on the nature and proportion of reactants required for carrying out such an alkoxylation reaction, or indeed what products can be obtained.

It has now been found that by using a specific ratio of alcohol to olefin, glycol ethers can be produced in the substantial absence of polyethylene glycol by-product.

Accordingly, the present invention is a process for making glycol ethers said process comprising reacting an olefin oxide with an alcohol over a catalyst comprising a crystalline metallosilicate which is basic in character, wherein the molar ratio of alcohol to olefin oxide employed is at least 2:1.

The olefin oxide used as reactant is suitably ethylene oxide, propylene oxide and/or a butylene oxide.

The alcohol used for the reaction is suitably a saturated, straight- or branched-chain, aliphatic, cycloaliphatic or aromatic alcohol and may be a mono- di- or poly-hydric alcohol, Monohydric alcohols are preferred. Specific examples of alcohols include the $C_1$–$C_6$ alcohols, especially, methanol, ethanol, the isomeric propanols and the isoineric butanols, particularly butan-1-ol. The alcohol is suitably used in a molar excess if the desired end product is a monoglycol ether. In general, the molar ratio of alcohol to the olefin oxide is preferably in the range from 4:1 to 15:1, most preferably in the range from 5:1 to 12:1.

The metallosilicates used as catalysts in the present invention have a generic composition in which the relative mole ratios of the various oxides may be as follows:

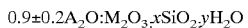

$0.9\pm0.2A_2O:M_2O_3.xSiO_2.yH_2O$ wherein A represents one or more alkali metal cations or a combination thereof with hydrogen ions, M represents a metal selected from aluminium, gallium, iron and boron, x is at least 2 and y/x is in the range from 0 to 25.

Thus, the crystalline metallosilicates used as catalysts in the process of the present invention are those of weakened acidity, and are basic in character. It is necessary to replace sufficient number of any hydrogen ions present in the metallosilicate with alkali metal ions such that the resultant metallosilicate is basic in character. It is preferable, however, to replace all of the hydrogen ions in the metallosilicate with alkali metal ions. The metallosilicates used are suitably aluminosilicates or gallosilicates. Within this range, metallosilicates in which M is aluminium are preferred. Metallosilicates in which the mole ratio of silica to $M_2O_3$ is in the range from 2:1 to 200:1 are most preferred. These metallosilicates are suitably of the large pore type with 12-membered rings pore systems having a pore size of about 7–8.5 Å. These are well known in the art and include inter alia the faujasites (eg zeolite Y, ultrastable zeolite Y (USY) dealuminated zeolite Y, ultrahydrophobic zeolite Y (UHP-Y), dealuminated silicon enriched zeolites such as LZ-210, zeolite X, CSZ-1 and CSZ-3 and ZSM-20, mordenite, zeolite-Beta, zeolite L and other similar natural or synthetic zeolites. A thorough description of the faujasite type zeolites can be found in Chapter 2 (pages 92–107) of Donald W Breck's "Zeolite Molecular Sieves", Robert E Krieger Publishing Co. (1984). Of these, particularly preferred are zeolites of the faujasite type (zeolites Y) and their ultrastable derivatives (zeolites USY). Where the metallosilicates are zeolites, these, in their as-synthesized form, are usually in the alkali metal ion-exchanged form. However, it may in some instances be necessary to convert this as-synthesized form into the corresponding hydrogen form in order to purify the as-synthesized zeolite, eg to remove extraneous aluminium impurities. In such an instance, the hydrogen form of the zeolite may have to be re-converted to the corresponding alkali metal ion exchanged form to derive metallosilicates which are basic in character. The hydrogen ions in these metallosilicates are exchanged for one or more alkali metal ion such as eg lithium, sodium, potassium, rubidium or caesium to derive the catalyst used in the present invention. Such an ion-exchange can be carried out by conventional techniques by treating the hydrogen form of the metallosilicate with a solution of an ionizable salt of the desired alkali metal such as eg the nitrate, chloride or carboxylate (eg acetate) of the alkali metal. This may typically be done by slurrying the crystalline metallosilicate in its hydrogen form with a solution of the alkali metal salt and leaving it in contact for a duration eg several hours, typically 12–100 hours. The contact between the metallosilicate in its acid form and the solution of the alkali metal salt, eg by slurrying, may have to be repeated several times to achieve the desired degree of ion exchange. When the resultant metallosilicate exhibits a basic character, it can be used as such or may prior to use be optionally washed several times with deionifed water until free from any extraneous ions, eg chlorides, nitrates etc, which may be detrimental to the catalytic activity of the metallosilicate for the desired reaction. Alternatively, the metallosilicate may be rendered basic by impregnating it with a solution of alkali metal compound which contains sufficient amount of basic cations to impart basicity to the metallosilicate. In this context, it may be desirable to have a stoichiometric excess of the alkali metal cations in the impregnating solution in order to increase the basicity of the metallosilicate. The resultant basic metallosilicate may be further activated by heating it in an air flow at elevated temperature eg from 250–650° C. for a few hours, eg 5–30 hours, before use as catalyst.

Prior to evaluation of the basic metallosilicate for its catalytic activity, the metallosilicate is suitably granulated using eg an infra-red press by pressing to about 10 tonnes and then crushing and sieving to an average particle size of range 0.5–1.0 mm. Furthermore, the catalyst particles are suitably calcined at an elevated temperature suitably form 150–350° C., typically about 160–180° C., under flow of a gas inert under the reaction conditions, eg nitrogen, at about 500 cm$^3$/min for several hours, eg 5–25 hours, typically about 15 hours before evaluation thereof for its activity.

The process of the present invention is suitably carried out in the liquid phase. The optimum reaction temperature will depend upon the reactants used but will generally be in the range from ambient to about 350° C. suitably from 80° C. to 330° C. The reaction can be carried out at a pressure in the range from atmospheric to about 50 bar (5000 KPa).

The process of the present invention can be used for instance for the reaction of butan-1-ol with one or more units of ethylene oxide to make butyl-monoglycol ether (BMGE), -diglycol ether(BDGE), -triglycol ether etc. The reaction proceeds particularly smoothly with very high selectivity when making the monoglycol ether.

The present invention is further illustrated with reference to the following

EXAMPLES

Example 1

Preparation of the Sodium Exchanged USY Zeolite

A USY zeolite (obtained from PQ Corporation, CBV780 Si/Al=80, 10 g) was exchanged at room temperature with 0.1M sodium nitrate solution (500 ml). The zeolite was exchanged four times; three exchanges which were performed for 24 hours and a fourth exchange period which lasted 96 hours.

After each exchange, the catalyst was filtered without rinsing and then re-slurried in fresh sodium nitrate solution. Upon completion of the last exchange, the catalyst was filtered and left unrinsed to prevent decationation. The catalyst was then dried at 100° C. overnight.

Preparation of Caesium Exchanged NaY Zeolite

The caesium-containing zeolite was prepared by contacting NaY zeolite (10 g, ex Toyo Soda grade No. HSZ-310NAA) with 0.1M caesium acetate solution (500 ml) at 40° C. for 24 hours. After each exchange the material was filtered, without washing and re-slurried in fresh caesium acetate solution. This procedure was performed three times. A fourth exchange was carried out over a 96 hours. After the last exchange the material was dried at 100° C. This catalyst was further activated in an air flow at 500° C. for 16 h before use.

Preparation of Caesium Exchanged Zeolite Beta

An extruded acid-form Beta zeolite (obtained from Zeolyst, CO 861E-22) was exchanged at 40° C. with 0.1M caesium acetate solution as described above in relation to the preparation of Caesium exchanged NaY zeolite Reactor System and Procedure.

Prior to catalytic evaluation all materials were granulated using an infra-red press by pressing to 10 tonnes and then crushing and sieving to a particle size of range 0.5–1.0 mm.

All catalytic testing was performed in a stainless steel fixed-bed flow reactor. Prior to the tests, all catalysts were calcined at 170° C. under a nitrogen flow of 500 cm$^3$/min for 16 hours.

Production of Glycol Ethers using Na-USY, NaY, CsNaY and Cs-Z-beta

The above catalysts were tested for the production of glycol ethers using, ethylene oxide and butan-l-ol. The catalyst bed volume used was 5 cm$^3$ in each case. The reaction was carried out using a mixed liquid feed which contained butan-1-ol and ethylene oxide. At the start of the reaction the reactor was pressurized to 30 barg (3100 KPa) at room temperature using the feed. When this reaction pressure had been attained and stabilized, the liquid feed was pumped into the reactor at the set rate of 5 cm$^3$/hour-(LHSV=1).

The reactor temperature was then slowly (at the rate of about 1° C. min$^{-1}$) increased to the reaction temperature of 150° C. Product sampling was performed at regular intervals.

The samples were analyzed using a Pye-Unicam 4500 gas chromatograph fitted with WCOT fused silica capillary column (50 m, 0.25 mm internal diameter, CP-Sil-5) operating with a temperature programme (80° C. for 10 minutes, ramping at the rate of 6° C. to 320° C.) to determine the relative amounts of the mono-glycol ether, higher-glycol ethers and by-products formed. Mass balances were typically 96% or higher for any test period. The liquid products were analyzed for monobutyl glycol ether, and also for di- and tri-substituted glycol ethers by gas chromatography and the results are shown in Table 1 below.

TABLE 1

| Catalyst | feed molar ratio of BuOH to EO | Ethylene oxide conversion* (mole %) | Selectivity to Glycol Ethers (% wt/wt) | | By-products (% wt/wt) |
| --- | --- | --- | --- | --- | --- |
| | | | Mono glycol ether | Di- and Tri- glycol ethers | |
| Na-USY | 5:1 | 40 | 92.8 | 4.9 | 2.3 |
| NaY | 8:1 | 53 | 92.2 | 5.4 | 2.4 |
| CsNaY | 7:1 | 72.2 | 86.8 | 12.6 | 0.6 |
| Cs-Beta | 8:1 | 91.4 | 86.0 | 10.7 | 3.2 |

*Ethylene oxide conversion is based on ethoxylated products only
*Cs-Beta = Caesium zeolite beta It can be seen from Table 1 that very high selectivities to the mono butyl glycol ether can be achieved using these catalysts. All tests were carried out for more than 200 hours on stream, and no deactivation of the catalyst was observed and substantially no polyethylene glycol—an undesirable by-product—was formed.

We claim:

1. A process for making glycol ethers, said process comprising reacting an olefin oxide with an alcohol over a catalyst comprising a crystalline metallosilicate which is basic in character, at a molar ratio of alcohol to olefin oxide of at least 2:1, wherein the crystalline metallosilicate is a zeolite in caesium ion exchanged form.

2. A process as claimed in claim 1, wherein the olefin oxide is selected from the group consisting of an ethylene oxide, propylene oxide and a butylene oxide.

3. A process as claimed in claim 1, wherein the alcohol is selected from the group consisting of methanol, ethanol, an isomeric propanol and an isomeric butanol.

4. A process as claimed in claim 3, wherein the alcohol is butan-1-ol.

5. A process as claimed in claim 1, wherein the molar ratio of alcohol to olefin oxide is from 4:1 to 15:1.

6. A process as claimed in claim 5, wherein the molar ratio of alcohol to olefin oxide is from 5:1 to 12:1.

7. A process as claimed in claim 1, wherein the metallosilicate is of the large pore type with 12-membered rings pore systems having a pore size of about 7–8.5 Å.

8. A process as claimed in claim 7, wherein the metallosilicate is selected from the group consisting of faujasite, mordenite, and zeolite-Beta.

9. A process as claimed in claim 1, which is carried out in the liquid phase.

10. A process as claimed in claim 1, which is carried out at a temperature of about ambient to about 350° C., and a pressure in the range from atmospheric to about 50 bar (5000 KPa).

* * * * *